United States Patent
Jue et al.

(10) Patent No.: US 12,329,520 B2
(45) Date of Patent: *Jun. 17, 2025

(54) CALIBRATION OF BLOOD GLUCOSE MEASUREMENT APPARATUS BASED ON RAMAN SPECTROSCOPY

(71) Applicant: Apollon Inc., Seoul (KR)

(72) Inventors: Miyeon Jue, Seoul (KR); Young Kyu Kim, Seoul (KR); Aram Hong, Seoul (KR)

(73) Assignee: Apollon Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/427,899

(22) Filed: Jan. 31, 2024

(65) Prior Publication Data

US 2024/0398273 A1    Dec. 5, 2024

Related U.S. Application Data

(63) Continuation of application No. 18/455,492, filed on Aug. 24, 2023, now Pat. No. 11,986,295.

(30) Foreign Application Priority Data

May 30, 2023    (KR) .................. 10-2023-0069417

(51) Int. Cl.
| | | |
|---|---|---|
| A61B 5/1455 | (2006.01) | |
| A61B 5/00 | (2006.01) | |
| A61B 5/145 | (2006.01) | |
| G01N 21/65 | (2006.01) | |
| G01N 33/49 | (2006.01) | |

(52) U.S. Cl.
CPC ........ *A61B 5/14532* (2013.01); *A61B 5/0002* (2013.01); *A61B 5/1455* (2013.01); *G01N 21/65* (2013.01); *G01N 33/49* (2013.01); *A61B 5/6801* (2013.01); *G01N 2201/061* (2013.01); *G01N 2201/127* (2013.01)

(58) Field of Classification Search
CPC ... A61B 5/0059; A61B 5/0075; A61B 5/1455; A61B 5/14551; A61B 5/14552; A61B 5/14532; A61B 5/68; A61B 5/6801
See application file for complete search history.

(56) References Cited

U.S. PATENT DOCUMENTS

| | | |
|---|---|---|
| 2005/0187439 A1 | 8/2005 | Blank |
| 2017/0135582 A1* | 5/2017 | Cho ............ A61B 5/725 |
| 2023/0277063 A1 | 9/2023 | Cucinelli |

FOREIGN PATENT DOCUMENTS

| | | |
|---|---|---|
| JP | 2018-530373 A | 10/2018 |
| JP | 2022-512369 A | 2/2022 |
| KR | 10-2018-0061959 A | 6/2018 |
| KR | 10-2408951 B1 | 6/2022 |

* cited by examiner

*Primary Examiner* — Chu Chuan Liu
(74) *Attorney, Agent, or Firm* — United One Law Group LLC; Kongsik Kim; Jhongwoo Peck

(57) ABSTRACT

Blood glucose level measurement includes a light source configured to irradiate light to a subject; a monochrome part configured to separate wavelength components of the light that is reflected and scattered from the subject; a light receiver configured to receive the light transmitted via the monochrome part and to generate electrical signals based on the received light; and a processor configured to extract information on the blood glucose level of the subject based on a frequency shift of the light due to the Raman effect.

8 Claims, 8 Drawing Sheets

CALIBRATION OF BLOOD GLUCOSE MEASUREMENT APPARATUS BASED ON RAMAN SPECTROSCOPY

CROSS-REFERENCE TO RELATED APPLICATIONS

This application is a Continuation of application Ser. No. 18/455,492 filed Aug. 24, 2023, which claims priority from Korean Application No. 10-2023-0069417 filed May 30, 2023. The aforementioned applications are incorporated herein by reference in their entireties.

RELATED ART

Embodiments of the inventive concept described herein relate to an apparatus for measuring blood glucose continuously based on Raman signal. More particularly, embodiments of the inventive concept relate to a blood glucose level measuring apparatus that may be mounted on a body of a user to non-invasively measure a blood glucose level.

A continuous blood glucose level measuring apparatus is a medical instrument that measures a blood glucose level of a patient for a corresponding time period and provides information to allow a patient to identify an increase/decrease trend of the blood glucose level and adjust a diet of the patient by himself or herself or determine an injection timing of a medicine, such as insulin.

For this reason, for more appropriate health management of diabetic patients, domestic and international diabetes and endocrine societies have revised their guidelines and recommend the use of continuous blood glucose level measuring apparatuses regardless of the type of diabetes.

In most of the commercially available continuous blood glucose level measuring apparatuses currently approved by the Food and Drug Administration (FDA) as medical devices, a needle of the measuring apparatus is injected into the patient and the blood glucose level measured by the needle is read through other devices such as smartphones.

Because the blood glucose level is measured in an invasive way using a needle, existing continuous blood glucose level measuring apparatuses are accompanied by pain when mounting the measuring apparatus, and side effects such as inflammatory reaction may be induced due to the invasive method of the needle, and long-term use of more than 15 days is impossible. Accordingly, to solve these disadvantages, a technique for non-invasively measuring blood glucose level is required.

SUMMARY

Embodiments of the inventive concept provide a continuous blood glucose level measuring apparatus that is mounted on a body of a user to non-invasively measure a blood glucose level.

Embodiments of the inventive concept provide a small-sized blood glucose level measuring apparatus that is mounted on a body of a user to measure a blood glucose level.

The problems to be solved by the inventive concept are not limited to the above-mentioned ones, and the unmentioned problems will be clearly understood by an ordinary person in the art from the following description.

According to an embodiment, a blood glucose level measuring apparatus utilizing a Raman spectrum includes a housing defining an interior accommodation space, a light source part disposed in the housing, and that irradiates light to a subject, a light receiving part disposed in the housing, and that receives the reflected and scattered light from the subject and acquires a Raman spectrum, and a processor disposed in the housing, and that extracts information on glucose, proteins, and fats of the subject by utilizing an area of a peak included in the Raman spectrum, and the processor is configured to perform a calibration by controlling the light source part and the light receiving part when the blood glucose level measuring apparatus starts to be driven or is mounted on a body of a user.

According to an embodiment, the processor may be configured to, when the calibration is performed, control the light source part such that light is output at a specific output for a specific time period, and set an amount and an exposure time period of light of the light source part when a blood glucose level is measured with reference to a peak corresponding to a specific Roman shift of a Raman spectrum acquired through the light receiving part for the specific time period.

According to an embodiment, the blood glucose level measuring apparatus may further include a communication part that transmits and receives data to and from an external terminal, an intensity of the Raman signal corresponding to the specific Raman shift may not reach a reference value even though the intensity of the Raman signal reaches a maximum output and a maximum exposure time period of the light source part when the calibration is performed, and the processor may be configured to control the communication part such that an error message is transmitted to the external terminal.

According to an embodiment, the intensity of the Raman signal corresponding to the specific Raman shift may be an intensity for a peak of 1450 $cm^{-1}$.

According to an embodiment, the light receiving part may include a diffracting grating that disperses the light reflected or scattered by the subject for wavelength bands, and a light detecting part that receives the light diffracted by the diffracting grating and convert the light into an electrical signal.

According to an embodiment, the light receiving part may include a filter array including a plurality of optical filters that transmits lights of different wavelength bands, a filter feeding part that feeds the filter array in one direction, and a light receiving part that receives the light that passed through the filter array and convert the light into an electrical signal.

According to an embodiment, the light receiving part may include a linear variable filter, of which wavelength bands of lights that pass through areas are different, a filter feeding part that feeds the filter array in one direction, and a light receiving part that receives the light that passed through the filter array and convert the light into an electrical signal.

According to an embodiment, the housing may include a contact surface contacting the subject, the contact surface may include a hole that causes the light emitted from the light source part to be emitted to an outside of the blood glucose level measuring apparatus, and causes the light reflected or scattered by the subject to be introduced into an interior of the blood glucose level measuring apparatus, and the hole may be formed at a central portion of the contact surface.

According to an embodiment, the blood glucose level measuring apparatus may further include a band coupled to the housing and that fixes the housing to the body of the user, and a battery formed to be detachably mounted on the band.

According to an embodiment, the blood glucose level measuring apparatus may further include an auxiliary battery that prevents the blood glucose level measuring apparatus from being switched to an off state when the battery is replaced, and disposed in the housing.

BRIEF DESCRIPTION OF THE DRAWINGS

The above and other objects and features will become apparent from the following description with reference to the following figures, wherein like reference numerals refer to like parts throughout the various figures unless otherwise specified, and wherein.

DETAILED DESCRIPTION

Figure 1:
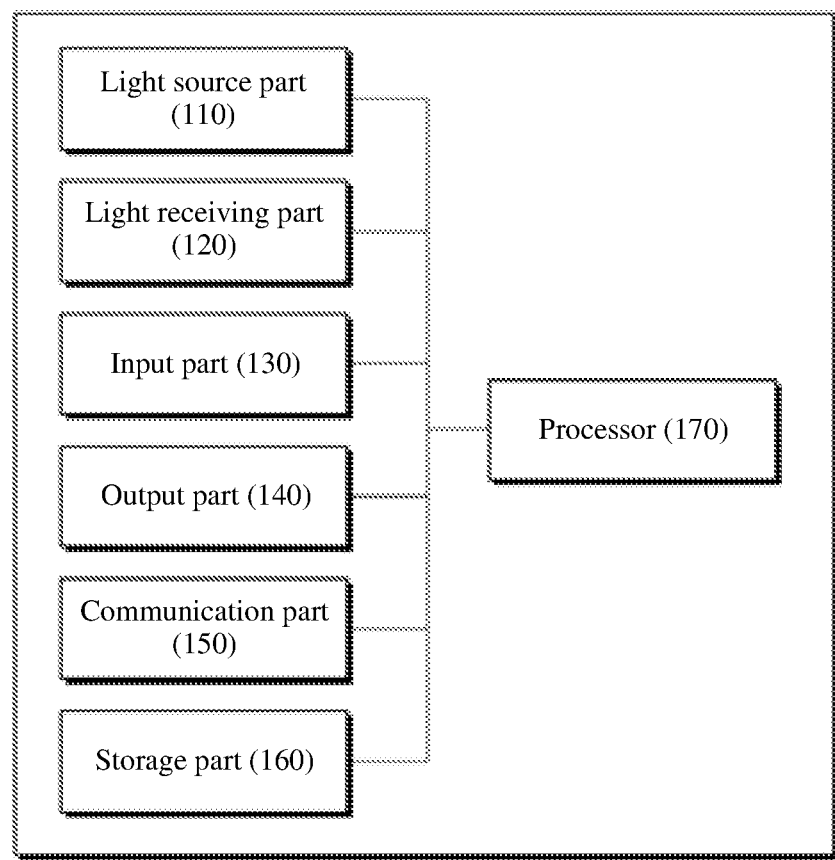
FIG. 1 is a block diagram illustrating a continuous blood glucose level measuring apparatus according to the inventive concept.

Throughout the inventive concept, the same reference numerals denote the same components. The inventive concept does not describe all components of embodiments, and a description of contents that are general in the field, to which the inventive concept pertains, and repeated contents of the embodiments will be omitted. The terms of 'part, module, member, and block' used in the specification may be implemented by software or hardware, and according to the embodiments, a plurality of 'parts, modules, members, and blocks' may be implemented by one component or one 'part, module, member, and block' may include a plurality of components.

Throughout the specification, when it is described that a certain part is "connected to" another part, this includes indirect connection as well as direct connection, and the indirect connection includes connection through a wireless communication network.

Furthermore, when it is described that a certain part includes a certain component, this means that another component may be further included while other components are not excluded unless described particularly in an opposite way.

Throughout the specification, when it is described that a certain member is located on another member, this includes a case, in which another member is present between the two members as well as a case, in which a certain member contacts the another member.

The terms of first, second, and the like are used to distinguish one component from another component, and the components are not limited by the above-described terms.

A singular expression includes a plural expression unless an exemption is explicitly described in the context.

Reference numerals are used for convenience of description in operations, and the reference numerals do not indicate the sequences of the operations and the operations may be carried out in other sequences than described unless a specific sequence is clearly described in the context.

Hereinafter, an operation principle and embodiments of the inventive concept will be described with reference to the accompanying drawings.

A continuous blood glucose level measuring apparatus according to the inventive concept may include a watch type, a wrist band type, a ring type, a belt type, a necklace type, an ankle band type, a thigh band type, and an arm band type. However, the inventive concept is not limited thereto, and the continuous blood glucose level measuring apparatus according to the inventive concept may be implemented in a form that may be fixed to a body of a user.

Figure 2:
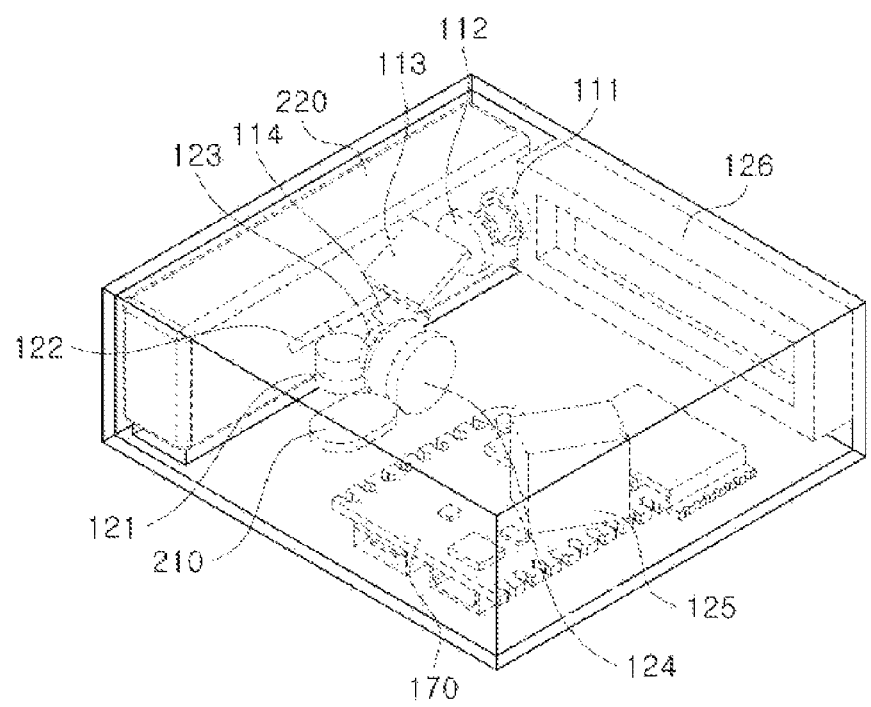
FIG. 2 is a perspective view illustrating an internal structure of a continuous blood glucose level measuring apparatus according to the inventive concept.
Figure 3:
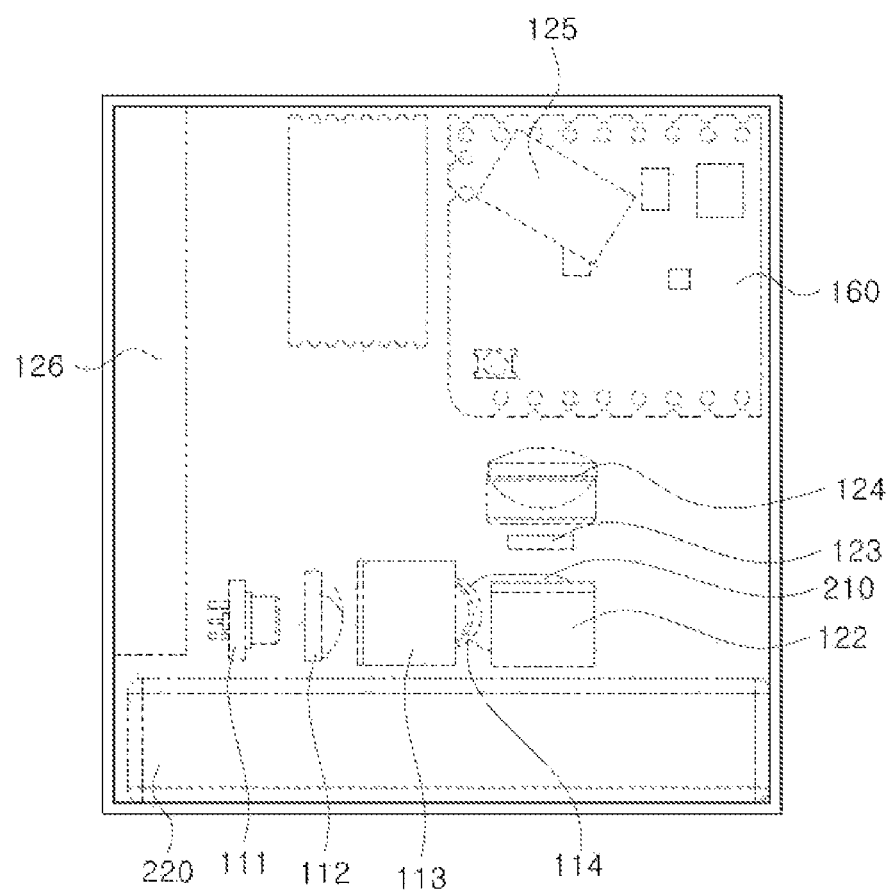
FIG. 3 is a plan view illustrating an internal structure of a continuous blood glucose level measuring apparatus according to the inventive concept.
Figure 4:
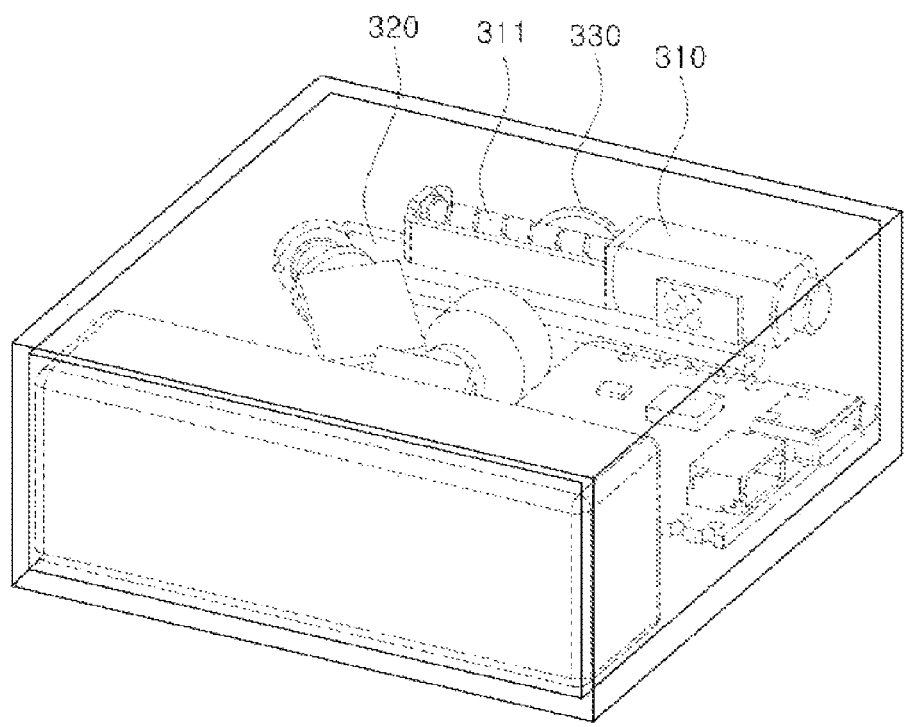
FIG. 4 is a perspective view illustrating an internal structure of a continuous blood glucose level measuring apparatus including an optical filter.
Figure 5:
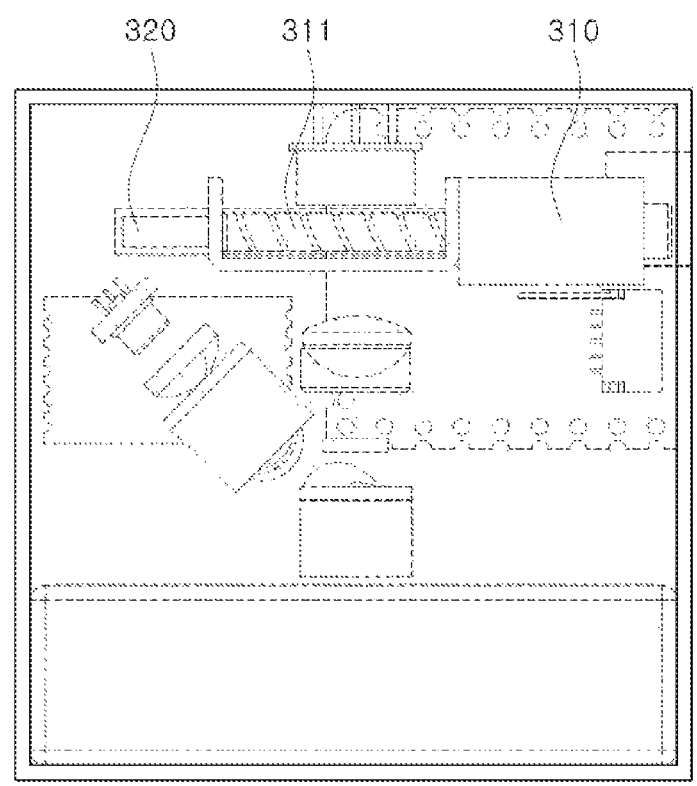
FIG. 5 is a plan view illustrating an internal structure of a continuous blood glucose level measuring apparatus including an optical filter.
Figure 6:
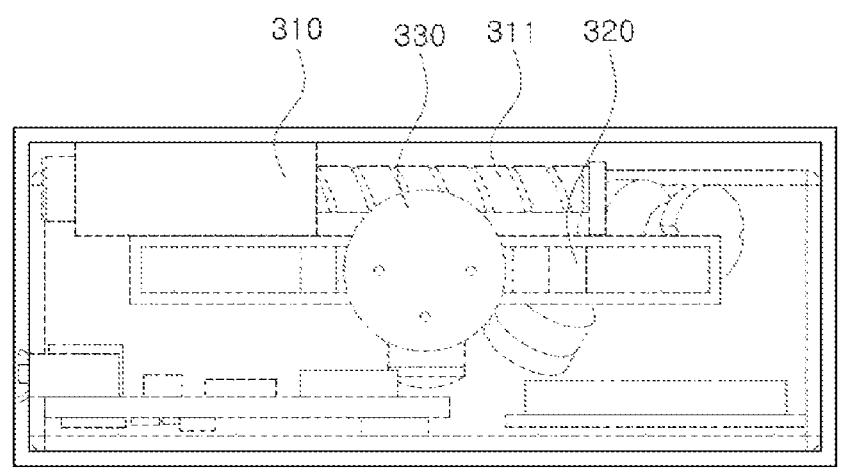
FIG. 6 is a side view illustrating an internal structure of a continuous blood glucose level measuring apparatus including an optical filter.

FIG. 1 is a block diagram illustrating a continuous blood glucose level measuring apparatus according to the inventive concept, FIG. 2 is a perspective view illustrating an internal structure of the continuous blood glucose level measuring apparatus according to the inventive concept, FIG. 3 is a plan view illustrating the internal structure of the continuous blood glucose level measuring apparatus according to the inventive concept, FIG. 4 is a perspective view illustrating the internal structure of the continuous blood glucose level measuring apparatus including an optical filter, FIG. 5 is a plan view illustrating the internal structure of the continuous blood glucose level measuring apparatus including the optical filter, and FIG. 6 is a side view illustrating the internal structure of the continuous blood glucose level measuring apparatus including the optical filter.

Referring to FIG. 1, the continuous blood glucose level measuring apparatus according to the inventive concept includes a light source part 110, a light receiving part 120, an input part 130, an output part 140, a communication part 150, a storage part 160, and a processor 170. However, the inventive concept is not limited thereto, and the continuous blood glucose level measuring apparatus according to the inventive concept may include components, the number of which is larger or smaller than the above-described components. Hereinafter, the above-described components will be described in detail.

The light source part 110 emits light and causes light to reach a subject (for example, skin). To achieve this, the light source part 110 may include at least one optical element of a light source that emits light, a lens that concentrates the emitted light to one site, an optical filter that filters some wavelength bands of the emitted light, a mirror that changes a travel direction of the emitted light, and a beam splitter that reflects a portion of the light and passes another portion thereof.

As described above, the light source part 110 includes the light source, and may include at least one optical element that changes at least one of a travel direction, a wavelength, a polarization, and an amount of the light emitted from the light source until the light reaches the subject. A detailed embodiment of the light source part 110 will be described below.

The light receiving part 120 receives the light reflected or scattered by the subject, and generate a Raman spectrum for analyzing a Raman signal. To achieve this, the light receiving part 120 may include at least one of a lens that concentrates the light reflected or scattered by the subject to one site, an optical filter that filters some wavelength bands of the light, a mirror that changes a travel direction of the light, and a spectroscope that disperses the light for each wavelength band and generates a spectrum of the light.

As described above, the light receiving part 120 may include at least one component for, to receive the light reflected or scattered by the subject and generate a Raman spectrum, generating a spectrum by changing at least one of a travel direction, a wavelength, a polarization, and an amount of the light or scattering the light for each wavelength band. A detailed embodiment of the light receiving part 120 will be described below.

The input part 130 is for receiving information from the user, and when information is input through the input part 130, the processor 170 may control an operation of the apparatus such that the operation corresponds to the input information. The input part 130 may include a hardware type physical key (for example, a button, a dome switch, a jog wheel, a jog switch, or the like that is located on at least one of a front surface, a rear surface, and a side surface of the apparatus), and a software type touch key. As an example, the touch key may include a virtual key, a soft key, or a visual key that is displayed on a touchscreen type display part through software processing, and may include a touch key that is disposed at a part, except for the touchscreen. Meanwhile, the virtual key or the visual key may be displayed on the touchscreen while having various forms, and for example, may include a graphic, a text, an icon, a video, or a combination thereof.

The output part 140 is for generating an output related to a visual, audible, or haptic feeling, and may include at least one of a display part, a sound output part, a haptic module, and a light output part.

The display part may have a layer structure with a touch sensor mutually or may integrally formed therewith to implement a touch screen. The touchscreen may function as a user input part that provides an input interface between the apparatus and the user, and may provide an output interface between the apparatus and the user as well.

The display part displays (outputs) information that is processed by the apparatus. For example, the display part may display execution screen information of an application program (as an example, an application) driven by the apparatus, or user interface (UI) or graphic user interface (GUI) information according to the execution screen information.

The sound output part may output audio data that are received through the communication part or are stored in the memory, or may output sound signals related to the functions performed by the apparatus. The sound output part may include a receiver, a speaker, or a buzzer.

The communication part 150 may include one or more components that allows communication with an external device, and for example, may include at least one of a wired communication module, a wireless communication module, and a short-range communication module.

The wired communication module may include not only various wired communication module, such as a local area network (LAL) module, a wide area network (WAN) module, or a value-added network (VAN) module but also various cable communication modules, a universal serial bus (USB), a high-definition multimedia interface (HDMI), a digital visual interface (DVI), a recommended standard 232 (RS-232), a power line communication, or a plain old telephone service (POTS).

The wireless communication module may include not only a Wi-Fi module and a wireless broad band module but also wireless communication modules that support global system for mobile (GSM) Communication, a code division multiple access (CDMA), wideband code division multiple access (WCDMA), universal mobile telecommunications system (UMTS), time division multiple access (TDMA), long term evolution (LTE), 4G, 5G, and 6G.

The short-range communication module is for short-range communication, and may support short-range communication by using at least one of Bluetooth, radio frequency identification (RFID), infrared data association (IrDA), ultra wideband (UWB), ZigBee, near field communication (NFC), wireless fidelity (Wi-Fi), Wi-Fi direct, wireless universal serial bus (USB) technologies.

The storage part 160 may store data that support various functions of the apparatus and programs for operations of the processor 170, may store data that are input and output, and may store application programs or applications that are driven by the apparatus, and data and instructions for operations of the apparatus. At least some of the application programs may be downloaded from an external server through wireless communication.

The memory may include at least one type of storage medium of a flash memory type, a hard disk type, a solid state disk (SSD) type, a silicon disk drive (SDD) type, a multimedia card micro type, a card type memory (for example, an SD or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, or an optical disk. Furthermore, the memory is separated from the apparatus, but may be a database that is connected to the apparatus by wire or wirelessly.

The processor 170 may be implemented by the storage part 160 that stores algorithms for controlling operations of the components of the apparatus or data for programs that implement the algorithms, and at least one processor that performs the above-described operations by using the data stored in the storage part 160. Then, the storage part 160 and the processor 170 may be implemented by separate chips. Alternatively, the storage part 160 and the processor 170 may be implemented by a single chip.

Furthermore, the processor 170 may control any one or a combination of the above-discussed components to implement various embodiments according to the inventive concept, which are described in FIGS. 2 to 8 below on the apparatus.

Meanwhile, the functions related to artificial intelligence according to the inventive concept are performed through the processor and the memory. The processor may include one or a plurality of processors. Then, the one or the plurality of processors may be a general-purpose processor, such as a CPU, an AP, or a digital signal processor (DSP), a graphic-specific processor, such as a GPU or a vision processing unit (VPU), or an artificial intelligence-specific processor, such as an NPU. The one or the plurality of processors perform a control to process input data according to predefined operation rules that are stored in the memory or an artificial intelligence model. Alternatively, when the one or the plurality of processors are artificial intelligence-specific processors, the artificial intelligence processors may be designed to have a hardware structure that is specified for processing of a specific artificial intelligence model.

The predefined operation rules or artificial intelligence models are made through learning. Here, an aspect that it is made through learning means that the predefined operation rules or the artificial intelligence models that are set to perform desired characteristics (or a purpose) by, a basic artificial intelligence model, perform learning by using a plurality of learning data through a learning algorithm. The learning may be performed directly by a device that performs artificial intelligence according to the inventive concept, and may be performed through a separate server and/or system. Examples of learning algorithms include supervised learning, unsupervised learning, semi-supervised learning, or reinforcement learning, but the inventive concept is not limited to the above-described examples.

The artificial intelligence model may include a plurality of neural network layers. The plurality of neural network layers may have a plurality of weight values, respectively, and perform neural network calculations through calculation results of previous layers and calculations of the plurality of weight values. The plurality of weight values of the plurality of neural network layers may be optimized by the learning results of the artificial intelligence model. For example, a plurality of weight values may be renewed such that loss values or cost values that are acquired by the artificial intelligence model during a learning process is decreased or minimized. The artificial neural network may include a deep neural network (DNN), and for example, includes a convolutional neural network (CNN), a deep neural network (DNN), a recurrent neural network (RNN), a restricted Boltzmann machine (RBM), a deep belief network (DBN), a bidirectional recurrent deep neural network (BRDNN), or a deep Q-network, but the inventive concept is not limited to the above-described examples.

According to an exemplary embodiment of the inventive concept, the processor may implement artificial intelligence. The artificial intelligence means an artificial neural network based machine learning scheme that simulates biological neurons of a person such that a machine performs learning. The methods for artificial intelligence may be classified into supervised learning, in which a solution (output data) of a problem (input data) is determined by providing the input data and the output data together as learning data, unsupervised learning, in which a solution (output data) of a problem (input data) is not determined in advance by providing only input data with no output data, and reinforcement learning, in which a reward is given by an external environment whenever a certain action is taken in a current state and learning proceeds to maximize the reward. Furthermore, the methods for artificial learning may be classified according to architectures that are structures for learning models, and architectures of a widely used deep learning technologies may be classified into a convolutional neural network (CNN), a recurrent neural network (RNN), a transformer), and a generative adversarial network (GAN).

The apparatus may include an artificial learning model. The artificial intelligence model may be one artificial intelligence model, and may be implemented by a plurality of artificial intelligence models. The artificial intelligence model may include a neural network (or an artificial neural network), and may include a statistic learning algorithm that mimics biological neurons in the machine learning and the cognitive science. The neural network may mean all of models that achieve problem solving capacities by changing synaptic coupling strengths of synapses through learning of artificial neurons (nodes) that form a network through synaptic couplings. The neurons of the neural network may include combinations of weight values or biases. The neural network may include one or more neurons or one or more layers including one or more nodes. As an example, the apparatus may include input layers, hidden layers, and output layers. The neural network that constitutes the apparatus may infer a result (an output) that is to be predicted from an arbitrary input by changing the weight values of neurons through learning.

The processor may generate a neural network, may train (or perform learning on) the neural network, may perform calculations based in the received input data, may generate information signals based on the performance result, or retrain the neural network. The models for the neural networks may include various kinds of models, such as a region with convolution neural network (R-CNN), a region proposal network (RPN), a recurrent neural network (RNN), a stacking-based deep neural network (S-DNN), a state-space dynamic neural network (S-SDNN), a deconvolution network, a deep belief network (DBN), a restricted Boltzman Machine (RBN), a fully convolutional network, a long short-term memory (LSTM) network, and a classification network, but the inventive concept is not limited thereto. The processor may include one or more processors for performing calculations according to the models of the neural networks. For example, the neural network may include a deep neural network.

It may be understood by an ordinary person that the neural network may include a convolutional neural network (CNN), a recurrent neural network (RNN), a perceptron, a multilayer perceptron, a feed forward (FF), a radial basis network (RBF), a deep feed forward (DFF), a long short term memory (LSTM), a gated recurrent unit (GRUM), an auto encoder (AE), a variational auto encoder (VAE), a denoising auto encoder (DAE), a sparse auto encoder (SAE), a Markov chain (MC), a Hopfield network (HN), a Boltzmann machine (BM), a restricted Boltzmann machine (RBM), a deep belief network (DBN), a deep convolutional network (DCN), a deconvolutional network (DN), a deep convolutional inverse graphics network (DCIGN), a generative adversarial network (GAN), a liquid state machine (LSM), an extreme learning machine (ELM), an echo state network (ESN), a deep residual network (DRN), a differentiable neural computer (DNC), a neural turning machine (NTM), a capsule network (CN), a Kohonen network (KN), and an attention network (AN), but is not limited and may include an arbitrary neural network.

According to an embodiment of the inventive concept, the processor may use various artificial intelligence structures and algorithms, such as a convolution neural network, such as GoogleNet, AlexNet, or a VGG network, a region with convolution neural network (R-CNN), a region proposal network (RPN), a recurrent neural network (RNN), a stacking-based deep neural network (S-DNN), a state-space dynamic neural network (S-SDNN), a deconvolution network, a deep belief network (DBN), a restricted Boltzman machine (RBN), a fully convolutional network, a long short-term memory (LSTM) Network, a classification network, generative modeling, explainable AI, continual AI, a representation learning, AI for material design, BERT for processing natural languages, SP-BERT, MRC/QA, Text Analysis, a dialog system, GPT-3, GPT-4, Visual Analytics for processing visions, Visual Understanding, Video Synthesis, Anomaly Detection for ResNet data intelligence, Prediction, Time-Series Forecasting, Optimization, Recommendation, or Data Creation, and the inventive concept is not limited thereto. Hereinafter, embodiments of the inventive concept will be described in detail with reference to the accompanying drawings.

Hereinafter, an implementation of a continuous blood glucose level analyzing apparatus including the above-described components will be described.

The components that will be described below may be disposed in a housing that defines an interior accommodation space.

Referring to FIGS. 2 and 3, a light source 111 may irradiate light to the subject. For example, the light source 111 may irradiate a near-infrared ray (NIR) or a mid-infrared ray (MIR) to the subject. However, a wavelength of the light emitted from the light source may be changed according to a purpose of measurement.

In an embodiment, the light source 111 may be a light emitting diode (LED) or a laser diode, but the inventive concept is not limited thereto.

The light emitted from the light source 111 may pass through a first lens 112 and is concentrated in a first mirror 113. The first lens 112 may concentrate the light emitted from the light source 111 to the first mirror 113. Through this, the first lens 112 may minimize a power consumption of a battery by eliminating a need to increase an output of the light source 111 to a specific level or more.

The light that passed through the first lens 112 is reflected by the first mirror 113. The reflected light passes a first wavelength plate 114. The first wavelength plate 114 includes a birefringent plate and changes a polarization direction of the light.

The light that passed through the first wavelength plate 114 is emitted to an outside of the continuous blood glucose level measuring apparatus through a hole 210. Here, the hole 210 may be formed on one surface of the housing. In detail, the housing includes a contact surface that contacts the subject, and the hole 210, through which the light emitted from the light source part is emitted to an outside of the blood glucose level measuring apparatus, and through which the light reflected or scattered by the subject is introduced into an interior of the blood glucose level measuring apparatus, is formed on the contact surface.

When the continuous blood glucose level measuring apparatus according to the inventive concept is mounted such that the contact surface contacts the body of the user, the light emitted to an outside reaches the subject (for example, skin).

The light that reached the subject is reflected or scattered and is introduced into the hole 210. The light introduced into the hole 210 passes through a second wavelength plate 121. The second wavelength plate 121 includes a birefringent plate and changes a polarization direction of the light. The light that passed through the second wavelength plate 121 is reflected by a second mirror 122.

The light reflected by the second mirror 122 passes through an optical filter 123. The optical filter 123 transmits only light of a preset wavelength band. Among the lights that are input to the optical filter 123, the light of wavelength bands other than the present wavelength band cannot pass through the optical filter 123.

The light that passed through the optical filter 123 is concentrated through a second lens 124. The light concentrated through the second lens 124 is input to a monochrome part 125. The light input to the monochrome part 125 is scattered for each wavelength bands and is input to a light detecting part 126. The monochrome part 125 according to the inventive concept may be implemented largely in two different forms.

First, the monochrome part 125 may be implemented in a scheme of dispersing light. In detail, the monochrome part 125 may be implemented in a form, in which the light is dispersed through a diffracting grating or a prism. In an embodiment, the monochrome part 125 may be a diffracting grating, and the light may be dispersed to a desired form by adjusting a size and an interval of the gratings.

The light detecting part 126 receives the light diffracted by the monochrome part 125 and converts the light to an electrical signal. The processor 170 may generate a Raman spectrum through the electrical signal. For example, the light detecting part 126 may be a charge coupled device (CCD), but the inventive concept is not limited thereto.

Second, the monochrome part 125 may be implemented in a scheme of interfering with a portion of the light to sort only a desired component. Referring to FIGS. 4 to 6, the monochrome part 125 may include a filter feeding part 310, an optical filter part 320, and a light receiving part 330.

The filter feeding part 310 rotates a rotation part 311 that is coupled to the filter feeding part 310. The filter array or a linear variable filter 320 is coupled to the rotation part 311 to be fed in one direction as the rotation part 311 is rotated. As the rotation part 311 is rotated in a first direction, the filter array or the linear variable filter 320 is moved in the first direction. As the rotation part 311 is rotated in a second direction that is opposite to the first direction, the filter array or the linear variable filter 320 is moved in the second direction that is opposite to the first direction. However, a means for feeding the filter array or the linear variable filter 320 in one direction is not limited to the above-described filter feeding part 310.

The filter array includes a plurality of optical filters that transmit lights of different wavelength band. When the filter array is moved in one direction in a state, in which the light is input to the filter array, the light receiving part 330 sequentially inputs the lights of different wavelength bands.

Here, the light receiving part 311 may be a charge coupled device (CCD), but the inventive concept is not limited thereto.

The linear variable filter is a filter, of which wavelength bands of lights that pass through areas are different. When the linear variable filter is moved in one direction in a state, in which the light is input to the linear variable filter, the lights of different wavelength bands are sequentially input to the light receiving part 330.

The filter feeding part 310 allows the filter array or the linear variable filter 320 to sequentially input the lights of desired wavelength bands to the light receiving part 330 by feeding the filter array or the linear variable filter 320 in one direction in a state, in which the light reflected or scattered by the subject is input to the filter array or the linear variable filter 320.

The processor 170 may generate a Raman spectrum by utilizing an electrical signal generated through the light of different wavelength bands, which are sequentially input.

In an embodiment, the continuous blood glucose level measuring apparatus according to the inventive concept may sort only signals of a necessary wavelength bands by using the filter array or the linear variable filter of a wavelength band (blood glucose level-specific signals: 911 $cm^{-1}$, 1060 $cm^{-1}$, 1125 $cm^{-1}$, 898 nm, 910 nm, and 915 nm, skin configuring protein-specific Raman signals: 1450 $cm^{-1}$ and 943 nm, and the like) that is changed by Raman scattering at 830 nm that is necessary for measuring a target material, and may cause the signals to reach the light receiving part 311. Through this, the inventive concept may minimize the continuous blood glucose level measuring apparatus by shortening a necessary optical path through use of a spectroscope.

The processor 170 generates a Raman spectrum based on the signals generated by the light detecting part 126. The Raman spectrum may be shown in a graph, in which the x axis represents a Raman shift (unit: $cm^{-1}$) and the y axis represents a signal intensity.

The processor 170 may measure a blood glucose level of the subject by analyzing the generated Raman spectrum. Before measuring the blood glucose level of the subject, the processor 170 may perform a calibration process on the blood glucose and the skin configuring protein-specific Raman spectrum.

In an embodiment, during the calibration, the processor 170 reduces noise through Savitzky-Golay filtering in the generated spectrum, and removes a background of the spectrum generated through polynomial fitting. A polynomial fitting order that is suitable for removing the background is determined based in intensities of fourth wavelengths, that is, the first wavelength, a wavelength at a point of two fourth, a wavelength at a point of three fourth, and the last wavelength.

Meanwhile, when driving of the apparatus is started, when the apparatus is restarted after the blood glucose level is measured, or when the apparatus is remounted after temporarily demounted, the processor 170 may perform a calibration again.

In an embodiment, the processor 170 may control the light source part such that the light is output at a specific output for a specific time period when the apparatus starts to be driven or is remounted, and may set an amount and an exposure time period of the light of the light source part when the blood glucose level is measured with reference to a peak corresponding to a specific Raman shift in the Raman spectrum acquired through the light receiving part for the specific time period.

Here, an intensity of the Raman signal corresponding to the specific Raman shift may be a peak of 1450 $cm^{-1}$.

When an intensity of the Raman signal corresponding to the specific Raman shift does not reach a reference value even though a maximum output and a maximum exposure time of the light source part are reached during the calibration, the processor 170 may control the communication part such that an error message is transmitted to the external terminal.

The user may identify the error message through the external terminal connected to the continuous blood glucose level measuring apparatus according to the inventive concept. The error message may include a text or an image that requests a change of an attachment portion or a reattachment.

Meanwhile, when a ratio of intensities of general Raman signal peaks and a ratio of intensities of the acquired Raman signal peaks are different by a specific reference or more, the processor 170 may determine that there is a contact error between the subject and the apparatus and may transmit an error message to the external terminal by controlling the communication part 150.

However, the inventive concept is not limited, and the processor 170 may display the error message through the output part 140 included in the continuous blood glucose level measuring apparatus while not transmitting the above-described error message to the external terminal.

Thereafter, the processor 170 may train the areas of the peaks of three elements, that is, glucose, proteins, and fats, and the glucose value at a time point of the measurement with data by utilizing a machine learning technique, such as deep learning utilizing partial least squares (PLS), Support Vector Machine (SVM), Autoencoder, ResNet, or the like, and the blood glucose level of the subject is continuously measured based on the trained model.

In an embodiment, the glucose level may be measured through finger blood sampling, vein blood sampling, or continuous CGM, but the scheme of measuring the glucose value is not limited thereto.

In an embodiment, the processor 170 estimates an amount of glucose in an interstitial fluid based on a ratio of an area of the peak having a central value of 1450 $cm^{-1}$ and an area of a peak of 1660 $cm^{-1}$ to an area of a peak of 1125 $cm^{-1}$.

Here, in a case of a peak having a central value of 1450 $cm^{-1}$, the area is obtained by using a range of 1415 $cm^{-1}$ to 1480 $cm^{-1}$ as a peak corresponding to proteins.

Meanwhile, in a case of a peak having a central value of 1660 $cm^{-1}$, the area is obtained by using a range of 1630 $cm^{-1}$ to 1685 $cm^{-1}$ as a peak corresponding to fats.

Meanwhile, in a case of the 1125 $cm^{-1}$ peak corresponding to glucose, the area can be obtained by using a total of three ranges. In detail, an area corresponding to glucose may be obtained by using 1089 $cm^{-1}$ to 1160 $cm^{-1}$ (a first range), 1115 $cm^{-1}$ to 1140 $cm^{-1}$ (a second range), and 1120 $cm^{-1}$ to 1130 $cm^{-1}$ (a third range).

Meanwhile, the continuous blood glucose level measuring apparatus according to the inventive concept includes a battery 220 for driving the above-described components.

As described above, because the continuous blood glucose level measuring apparatus according to the inventive concept may continuously measure the blood glucose level in a non-invasive way, side effects are significantly less when mounted than an existing continuous blood glucose level measuring apparatus, which necessarily requires needle injection.

Hereinafter, various embodiments of the continuous blood glucose level measuring apparatus according to the inventive concept will be described.

Figure 7:
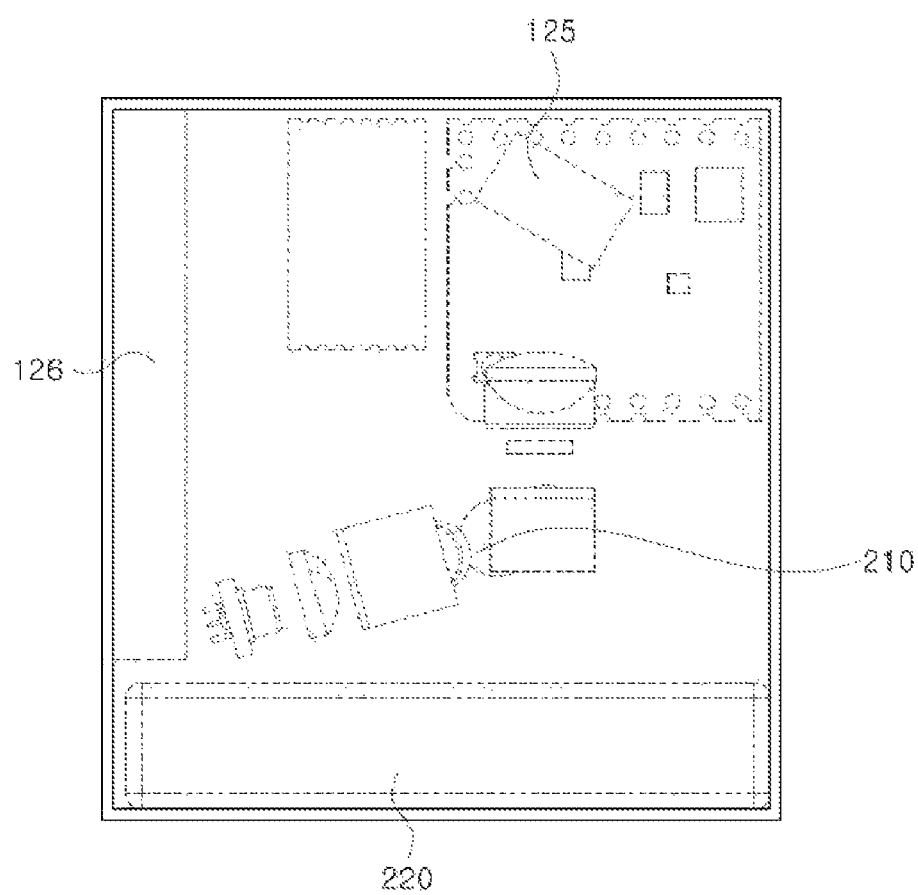
FIG. 7 is a plan view illustrating an internal structure of a continuous blood glucose level measuring apparatus, in which a hole is located at a central portion thereof.

FIG. 7 is a plan view illustrating an internal structure of the continuous blood glucose level measuring apparatus, in which a hole is located at a central portion thereof.

In the design of the conventional spectrometer for generating a Raman spectrum, a shape, in which a hole is disposed at an outskirt of a corner rather than in a center of the apparatus, is used because a stable optical path for securing a light dispersion angle of a monochrome part has to be secured.

However, it is preferable that the hole is disposed at a central portion of the body. In case of a wearable device that is fixed to the body of the user, the body of the device and the body of the user may be spaced apart from each other according to an activity of the user. Because a central portion of the body of the wearable device is attached to the body of the user strongest, a distance between the light source part and the subject may be constantly maintained more stably as the hole is located to be closer to a central portion of the contact surface of the housing.

To achieve this, referring to FIG. 7, according to the inventive concept, the hole 210 may be disposed at a central portion of the contact surface included in the housing, the light detecting part 126 and the internal battery 220 may be disposed at an outermost outskirt of an interior of the body, and the light source may be disposed toward the hole 210 disposed at a central portion of the contact surface. Accordingly, an angle between a path of the light that is input from the light source to the first mirror and a path of the light that is input to the monochrome part 125 becomes larger than 90 degrees.

As a result, the continuous blood glucose level measuring apparatus according to the inventive concept has a light dispersion angle and an optical path that are insufficient, and thus a measured wavelength band becomes smaller. The inventive concept solves a problem of a narrow measured wavelength band by selectively analyzing only the blood glucose level-specific wavelength band. Through this, according to the inventive concept, the hole may be disposed at a central portion of the contact surface of the subject provided in the housing.

As described above, according to the inventive concept, an accuracy in measurement of the blood glucose level may be increased by locating the hole, through which the light irradiated from the subject is emitted, at a central portion of the apparatus.

Meanwhile, according to the inventive concept, the battery may be replaced while the measurement of the blood glucose level is not ended.

Figure 8:
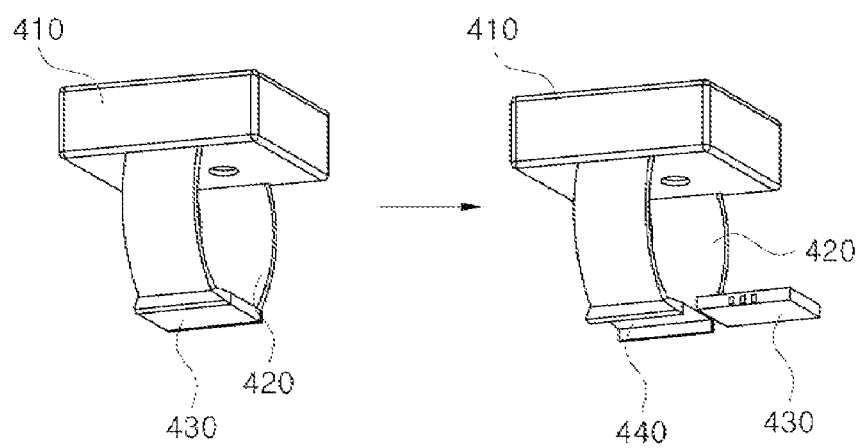
FIG. 8 is a conceptual view illustrating a band type continuous blood glucose level measuring apparatus.

FIG. 8 is a conceptual view illustrating a band type continuous blood glucose level measuring apparatus.

The continuous blood glucose level measuring apparatus according to the inventive concept may be implemented in a form of a band that may be fixed to a wrist, a wrinkle, an arm, or the like. To achieve this, the continuous blood glucose level measuring apparatus may include a housing 410 and a band 420.

Moreover, the continuous blood glucose level measuring apparatus according to the inventive concept may include a battery 430. The battery 430 may be disposed at a location that is different from that of the housing 410. As an example, the battery 430 may be disposed in an opposite direction to the housing 410.

Meanwhile, a circuit that electrically connects the battery 430 and the components in the housing 410 may be disposed in the band 420.

The battery 430 may be formed to be detachably mounted on the band 420, and to achieve this, the band may include a battery fastening part 440. The battery fastening part 440 fixes the battery 430 to the band, and electrically connects the battery 430 and a circuit disposed in the band 420.

Meanwhile, an auxiliary battery may be disposed in the housing 410. The auxiliary battery allows the continuous blood glucose level measuring apparatus to maintain its function while the battery 430 is replaced.

A calibration has to be performed when the blood glucose level starts to be measured after the battery is replaced, while it is switched to an off state when the battery is replaced. Accordingly, a gap may occur in the blood glucose level measurement time period, and the user has an inconvenience of having to perform a calibration every time the battery is replaced.

According to the inventive concept, a convenience of the user may be increased by preventing the apparatus from switched to an off state even when the battery is replaced.

Meanwhile, the disclosed embodiments may be implemented in a form of a recording medium that stores instructions that are executable by a computer. Instructions may be stored in a form of program codes, and when being executed by a processor, program modules may be generated to perform operations of the disclosed embodiments. The recording medium may be implemented as a computer-readable recording medium.

Computer-readable recording media include all types of recording media, in which instructions that may be decoded by a computer are stored. For example, there may be a read only memory (ROM), a random access memory (RAM), a magnetic tape, magnetic disk, a flash memory, an optical data storage device, and the like.

According to the above-described solutions of the inventive concept, because the continuous blood glucose level measuring apparatus according to the inventive concept may continuously measure a blood glucose level in a non-invasive way, side-effects are less as compared with an existing continuous blood glucose level measuring apparatus, in which a needle is essentially injected.

Furthermore, according to the inventive concept, degradation of an accuracy of measurement of a blood glucose level during mounting of the apparatus may be avoided.

The disclosed embodiments have been described with reference to the accompanying drawings. It will be understood by an ordinary person in the art, to which the inventive concept pertains, that the inventive concept may be carried out in a form that is different from the disclosed embodiments while not changing the technical spirits or essential features of the inventive concept. The disclosed embodiments are exemplary, and should not be construed in a limited way.

What is claimed is:

1. An apparatus for measuring blood glucose level, comprising:
a light source configured to irradiate light to a subject;
a monochrome part configured to separate wavelength components of the light that is reflected and scattered from the subject;
a light receiver configured to receive the light transmitted via the monochrome part and generates electrical signals representative of a Raman spectrum based on the received light; and
a processor configured to extract information on the blood glucose level of the subject based on the Raman spectrum,
wherein the processor is configured to perform a calibration by:
controlling the light source to irradiate the light at a predetermined output for a predetermined duration; and
determining an intensity and an exposure duration for the light to be irradiated by the light source to subsequently measure the blood glucose level of the subject based on a peak corresponding to a specific Raman shift of the Raman spectrum acquired via the light receiver during the calibration.

2. The apparatus of claim 1, wherein during the calibration, the processor is configured to reduce noise in the Raman spectrum based on Savitzky-Golay filtering, and to remove a background of the Raman spectrum by a polynomial fitting.

3. The apparatus of claim 2, wherein an order of the polynomial fitting is selected to be suitable for removing the background and is determined based on intensities of four wavelengths, which includes a first wavelength, a wavelength at a point of two quarters, a wavelength at a point of three quarters, and a last wavelength.

4. The apparatus of claim 1, wherein the peak corresponding to a specific Raman shift is at 1450 $cm^{-1}$.

5. The apparatus of claim 1, wherein, in response to an intensity of the peak corresponding to a specific Raman shift not reaching a predetermined threshold intensity level even with a predetermined maximum output and a predetermined maximum duration of the light source, the processor is configured to cause an error message to be transmitted.

6. The apparatus of claim 1, wherein, in response to a ratio of intensities of general Raman signal peaks and a ratio of intensities of signal peaks of the Raman spectrum are different by a predetermined threshold or more, the processor is configured to determine that there is a contact error between the subject and the apparatus and to cause an error message to be transmitted.

7. The apparatus of claim 1, wherein the calibration is performed in response to the apparatus being switched from an off-state to an on-state.

8. The apparatus of claim 1, wherein the calibration is performed in response to the processor determining that the apparatus is mounted on a body of the subject.

* * * * *